United States Patent [19]

Gustavsson

[11] Patent Number: 4,564,054
[45] Date of Patent: Jan. 14, 1986

[54] FLUID TRANSFER SYSTEM

[76] Inventor: Bengt Gustavsson, Bergsbogatan 29, Västra Frölunda, Sweden, 421079

[21] Appl. No.: 606,184

[22] Filed: May 2, 1984

Related U.S. Application Data

[63] Continuation-in-part of Ser. No. 536,647, Sep. 28, 1983, abandoned.

[30] Foreign Application Priority Data

Mar. 3, 1983 [SE] Sweden ................................ 8301176

[51] Int. Cl.⁴ ................................................. B65B 3/04
[52] U.S. Cl. ...................................... 141/329; 604/198; 604/411; 141/383
[58] Field of Search ................. 141/19, 329, 330, 286, 141/382–386; 604/411, 414, 198, 192, 201, 253

[56] References Cited

U.S. PATENT DOCUMENTS 4,201,208 5/1960 Cambio .............................. 604/411

Primary Examiner—Houston S. Bell, Jr.
Attorney, Agent, or Firm—Holman & Stern

[57] ABSTRACT

A device is disclosed for preventing air contamination when transferring a substance from one vessel to a second vessel. The device is attached or connectible to the vessel and comprises a first member, in which a puncturing member e.g. a needle, provided with a passage is enclosed. The first member has a sealing member, e.g. a membrane, through which the needle can be passed. The device further comprises a second chamber, which is detachably connectable to the first member and which also has a sealing member, e.g. a membrane. When the first and second members are connected to each other the two sealing members are located in a position with respect to each other so that they can be penetrated by the puncturing member which is movable with respect to the sealing members.

27 Claims, 20 Drawing Figures

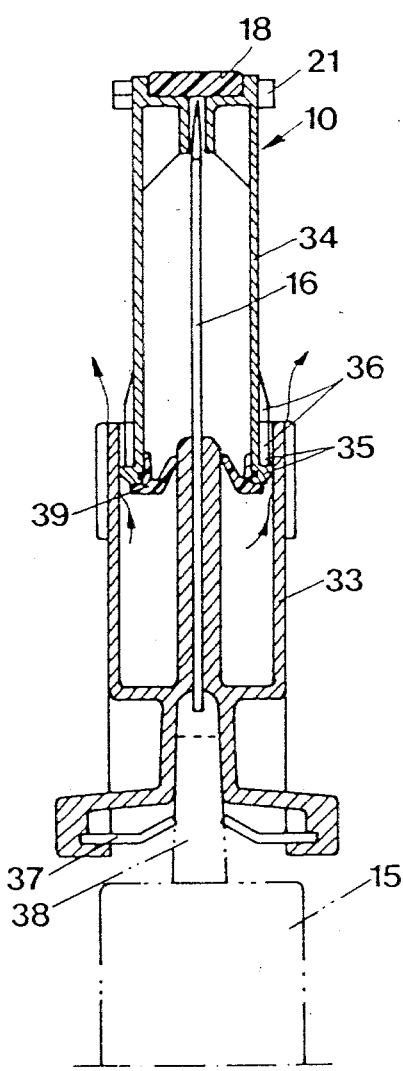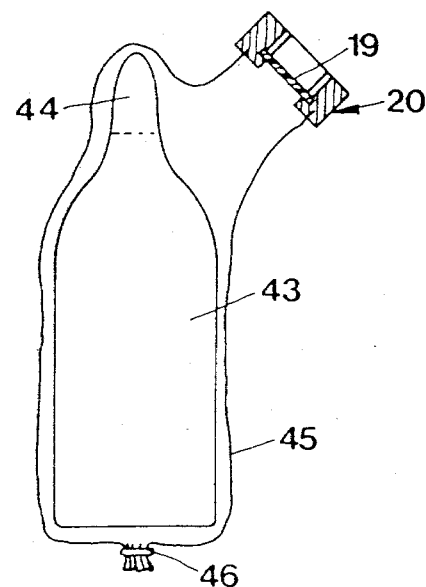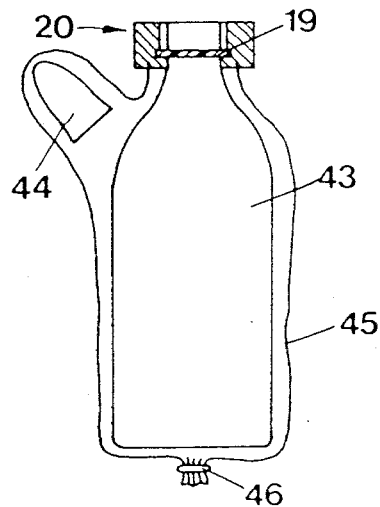

FLUID TRANSFER SYSTEM

This application is a continuation-in-part of the U.S. Ser. No. 536,647 filed Sept. 28, 1983 which is now abandoned.

TECHNICAL FIELD

The present invention relates to a device for preventing air contamination when handling chemicals. More particularly, the present invention relates to a device attached or connectible to a first vessel or a cover enclosing this and comprises a first member in which a puncturing member, e.g. a needle, provided with a passage is enclosed, said first member having a sealing member, e.g. a membrane through which the puncturing member can be passed.

BACKGROUND OF THE INVENTION

On injection of a substance directly into a patient or via an infusion aggregate one cannot avoid contamination of the air through formation of aerosols or drops. This happens partly during drawing in the medium from the ampoule, in which it is normally contained, to the injection syringe, and partly in connection with the injection itself into the patient or the infusion bottle. This air contamination leads to problems among other things in the form of allergic reactions in the exposed personnel, especially when it is a question of cytotoxic drugs, anaesthetics, media containing isotopes and allergy inducing substances of various kinds.

The same problem with air contamination occurs during handling of poisonous chemicals, for example solvents of different types, in industries, in laboratories, etc.

There are previously known devices for transferring a medicine in liquid form from an ampoule to a bottle without contamination. Such an apparatus is shown for example in the Norwegian Pat. No. 141,537 and it contains a double needle, one end of which is protected by an elastic hood, which the needle can penetrate by pressing together the hood, whereby the needle can be inserted into an ampoule. The opposite end of the needle is pushed through the membrane to a bottle with an infusion solution. This device presupposes that the medicine is already in the ampoule as a solution and therefore need not be dissolved first. Further there is no possibility of using the apparatus without contamination risk to inject the medicine directly into the patient.

SUMMARY OF THE INVENTION

The purpose of the present invention is to provide a device of the type previously mentioned and with which one can transfer without contamination a substance from a vessel to the desired application, for example injection into a patient or other application. This has been achieved by the fact that the apparatus further comprises a second member, to which said first member is detachably connectible and which also is provided with a second sealing member, e.g. a membrane, whereby the two sealing members in the connected position of the first and second members are located in a position with respect to each other, so that they can be penetrated by the puncturing member, which is movable relative to the sealing members.

DESCRIPTION OF THE DRAWING

In the following the invention will be described in detail with reference to some embodiments shown in the attached drawings.

FIG. 4 is a section showing the first member of the device in position for coupling to a third member, which is attached to a cannula, vein catheter or the like.

FIGS. 7–19 are sections through further embodiments of the device or parts thereof.

DESCRIPTION OF EMBODIMENTS

Figure 1:
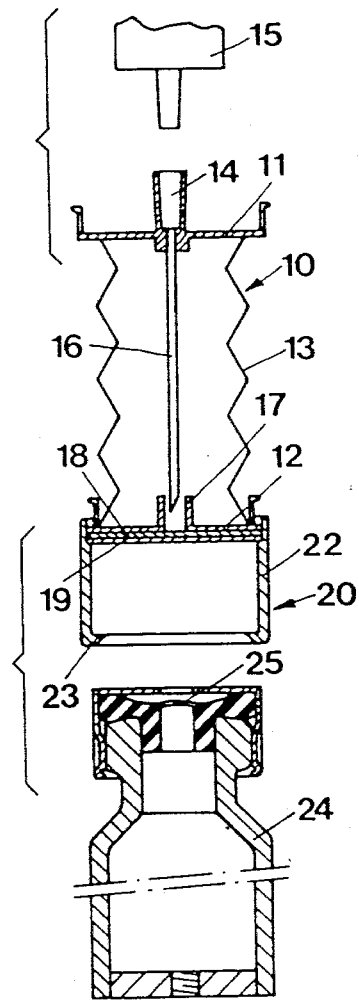
FIG. 1 is a vertical section through a device according to the invention and an injection syringe and ampoule for connection to the device.
Figure 2:
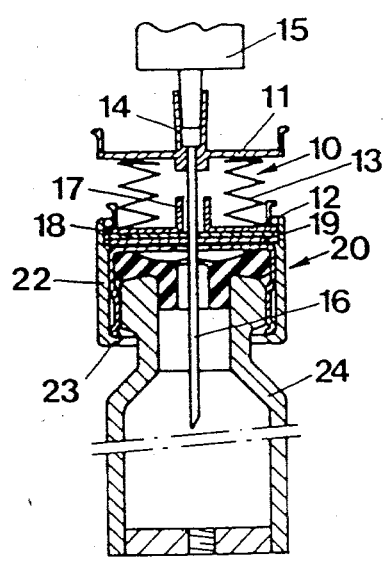
FIG. 2 is a corresponding section showing the device attached to the injection syringe and ampoule and in a position where the needle is inserted into the ampoule.
Figure 3:
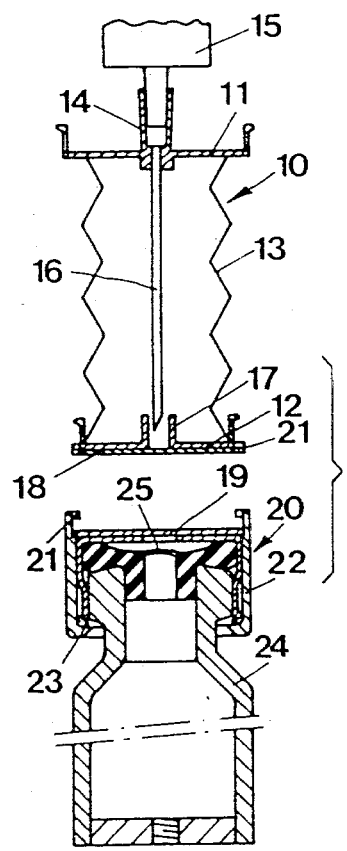
FIG. 3 is a corresponding section but in a position where the first member of the device is uncoupled from the ampoule.

The device according to the embodiment shown in FIGS. 1–3 comprises two detachably coupled together members, of which the first 10 contains two plates 11 and 12 spaced from each other and which are connected through flexible side walls 13. On the first plate 11 there is provided an attachment piece 14 for an injection syringe 15. On the inside of the plate is further fastened a puncturing member in the form of a needle 16 with a passage, which communicates with the attachment piece 14. The other plate 12 has a passage for the needle 16, and a guide 17 for it. The needle 16 extends to said guide 17. A first membrane 18 is placed for apposition against the outside of the second plate 12.

The second member 20 of the device, which is connected to the first member 10 by a bayonet coupling 21, Luer lock coupling or the like contains a second membrane 19, which is placed in tight apposition against the first membrane 18. The membrane 19 is fastened in a ring shaped part 22, which on top is terminated by the coupling part to the first member 10 and on the bottom is terminated by an inwardly directed flange 23, so that part 20 can be snap fastened on an ampoule 24 containing a dry substance or a solution. The membranes 18 och 19 are appropriately made of Teflon ®—material, which seals itself tight after penetration. The membranes could also be provided with preformed holes, through which a puncturing member can be passed. The tip of the puncturing member does in this case not need to be sharp.

By pressing together the flexible side walls 13 axially, as shown in FIG. 2, the needle 16 penetrates the two membranes 18 and 19 and the rubber membrane 25 of the ampoule 24 and is inserted into the ampoule. If this contains a dry substance this can be dissolved by a solvent contained in the injection syringe and thereafter can be sucked up into the injection syringe. If the ampoule contains medicine in solution this is directly sucked up into the injection syringe 15.

When the substance has been sucked up into the injection syringe 15 the needle 16 is withdrawn through the membranes 18 and 19 and the second member 20 is allowed to remain on the ampoule 14 while the first member 10, which is attached to the injection syringe 15 is detached, as is shown in FIG. 3. The second membrane 19 makes a tight seal to the ampoule 24 and is appropriately thrown away with it. The substance can now either be injected directly into a patient or be added into an infusion bottle. In order to avoid air contact also at this step a third member 32 (FIG. 4) is arranged, one end of which is attached or connectible to the patient's cannula 26 or vein catheter or to the infusion bottle and the opposite end of which is connectible to the first member 10 in a corresponding way as the second member 20. If the substance is intended to be added to an infusion bottle the member 32 can be provided with a cannula, with which the membrane of the infusion bottle is penetrated, after which the first member 10 is connected. The third member also has a membrane 27 of the same type as the membranes 18 and 19. The membranes 18 and 27 are brought to tight apposition against each other when the members 10 and 32 are attached to each other. The needle 16 penetrates the membranes 18 and 27 by pressing together the flexible side walls 13 in the axial direction. When the injection is terminated the needle 16 is withdrawn through the membranes 18 and 27, which seal tightly again. The injection syringe 13 with the attached part 10 is then thrown away.

Air contact is avoided in this way completely from the transfer of the substance from the ampoule to the injection syringe and to injection into the patient or the infusion bottle.

Figure 5:
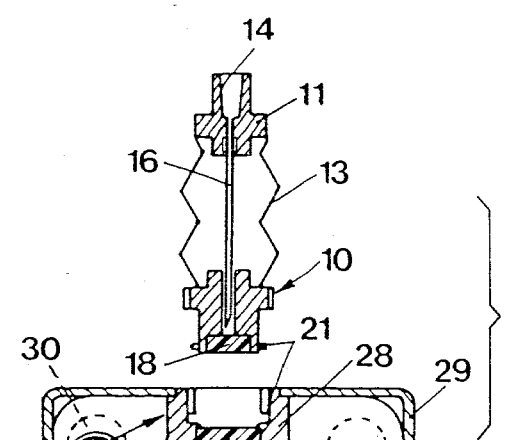
FIG. 5 is a section through a modified variant of an ampoule equipped with a pressure equalization bladder and with a device according to the invention.

In FIG. 5 is shown a modified variant of the device according to the invention, where the second member 20 is integral with the closure means 28 of an ampoule 24. The membrane 19 is placed in an opening in the closure means 28, which also has a coupling means, for example an bayonet coupling 21, for the first member 10. The closure means 28 is covered by a hood 29 of metal, plastic or the like, under which is placed a torus-shaped expandable bladder 30, which via a tube or a needle 31 through the closure means 28 communicates with the interior of the ampoule 24. It would also be possible to provide the closure means 28 with a piece of tube (not shown) extending into the ampoule and through which the needle 16 can be passed. Said tube would be provided with a radial opening which via a passage through the stopper communicates with the bladder 30. A cylindrical bladder attachment with a liquid-rejecting filter is denoted with the numeral 32.

The bladder works as a pressure equalizer when handling the contents of the ampoule. If the ampoule contains a dry substance this must first be dissolved in a solvent, for example water, which is injected with an injection syringe. The air pushed out is then pressed into the bladder 30. To avoid liquid to enter the bladder 30 a filter can be placed between it and the tube or needle 31. On sucking up the dissolved substance into the injection syringe air is sucked back into the ampoule from the bladder 30. A completely closed pressure equalization system has thus been achieved. The bladder 30 can of course be arranged in other ways, for example as a balloon which hangs down below the hood 29, which in this case can be made smaller. I would also be possible to arrange a pressure equalizing bladder attached to the first member.

Figure 6:
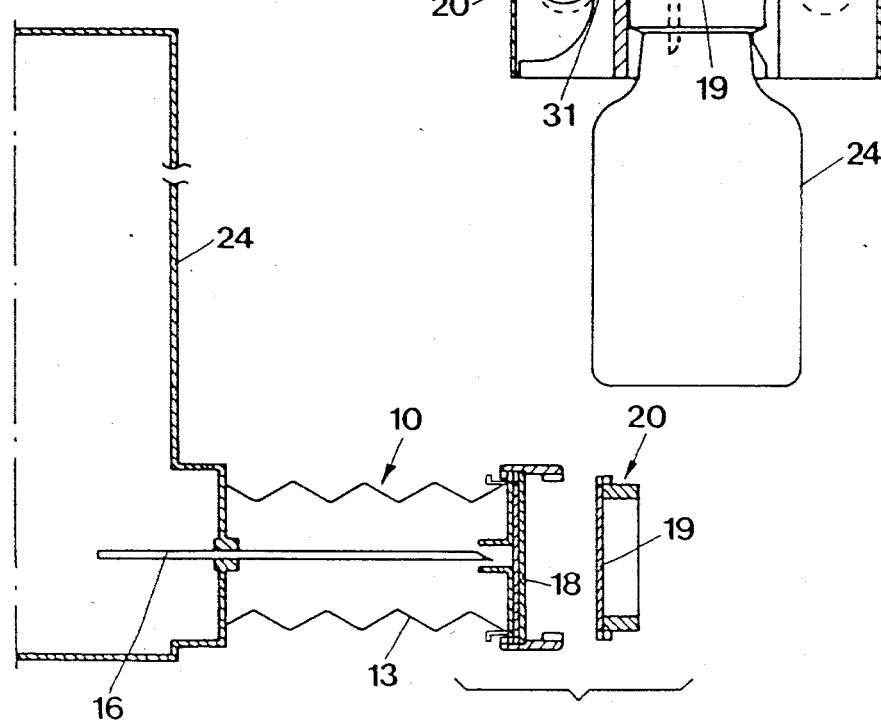
FIG. 6 is section through an additional embodiment of the device attached to a large storage vessel containing for example a solvent.

In FIG. 6 is shown an embodiment designed for handling poisonous chemicals, for example solvents, in laboratories, in industries etc. The first member 10 of the device is here attached to a large vessel 24 containing for example a solvent. The needle 16 extends into the container 24. When the solvent is to be taken out of the vessel 24 the second member 20 of the device is connected to a second vessel, whereupon the members 10 and 20 are coupled together and the flexible side walls 13 are pressed together so that the needle 16 penetrates the membranes 18 and 19.

In FIG. 7 is shown an embodiment, in which the first member 10 comprises a pair of telescoping parts, the outer 33 of which having e needle 16 attached thereto and being arranged to receive an injection syringe 15. The inner part 34 is provided with a first membrane 18 at its end facing away from the outer part 33 and is arranged to be coupled together with the second member 20 of the device, e.g. in a corresponding manner as is shown in FIG. 5 by means of a bayonet coupling 21 or the like. The telescoping parts 33 and 34 are each provided with stop lugs 35 preventing the parts from being separated from each other. At the end portions facing each other the telescoping parts 33 and 34 are fluted 36 in the axial direction for preventing the parts from being rotated relative to each other in the most extended position. The injection syringe 15 is firmly locked to the outer part 33 by means of a disc 37 of e.g. metal attached to said part and provided with a central slotted opening with sharp edges and into which the conical connection piece 38 is passed, at which the the material portions between the slots will be bent upwards as seen in FIG. 7. An attempt to withdraw the injection syringe 15 from the part 33 will result in that the sharp edges surrounding the opening in the disc 37 will be pressed into the walls of the connection piece 38 and a withdrawal is effectively prevented. A lip sealing 39 is attached to the inner part 34 and which seals between the interior of the inner part 34 and the outer part 33. Air is admitted to pass between the telescoping parts 33 and 34 as is indicated with arrows in FIG. 7. The second member of the device can e.g. be of the kind shown in FIG. 5.

Figure 8:
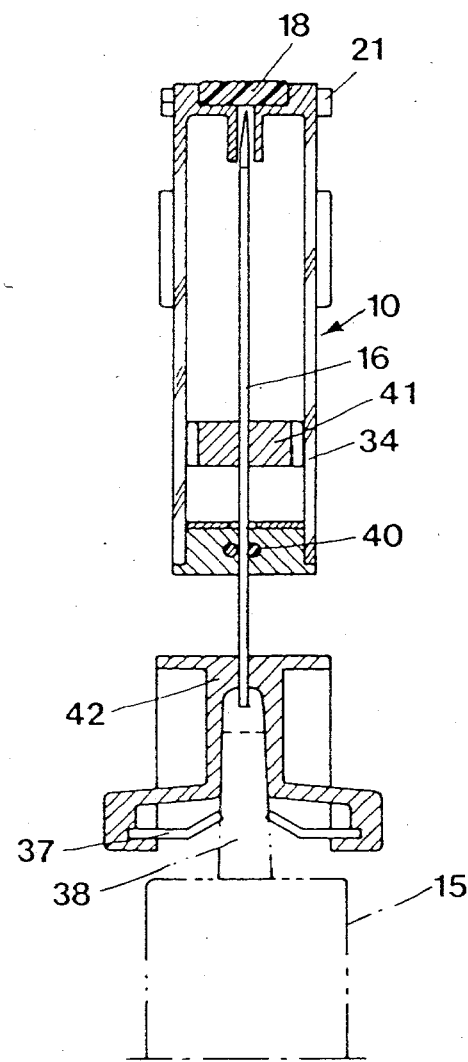

In FIG. 8 is shown a further embodiment, in which the needle 16 is displaceably received in the first member 10 and sealed against this by a sealing 40. The needle is provided with a ventilated piston guide 33, which is guided against the inside of the first member 10, which in this case is designed as a cylinder. The needle 16 is fixed to a connection piece 42, to which the injection syringe 15 can be undetachably connected in the corresponding way as in the embodiment according to FIG. 7. The second member 20 of the device can e.g. be of the kind shown in FIG. 5.

In FIGS. 9a–b is shown how the device can be applied on substances delivered in sealed ampoules 43. These are at the neck provided with a weakening 44, at which it easily can be broken off by hand. The unbroken ampoule 43 is placed in a bag or casing 45 of a pliable, strong and preferably transparent material and which after that is closed by a seal 46 (FIG. 9a). The ampoule is broken at the weakening 44 when located in the bag 45. The bag 45 is provided with a connection member corresponding to the second member 20 and to which the first member 10 can be connected. The ampoule is moved in the bag 45 so that its opening will be located just opposite and connected to the second member 20, while its broken-off end 47 remains beside the ampoule (FIG. 9b). Alternatively the bag 45 is only provided with a connection member to which the second member 20 can be coupled. The transfer of the substance from the ampoule 43 to e.g. an injection syringe connected to the first member 10 is performed in exactly the same way as is described above by bringing the needle 16 to penetrate the membranes 18 and 19 and be inserted into the ampoule 43.

Figure 10:
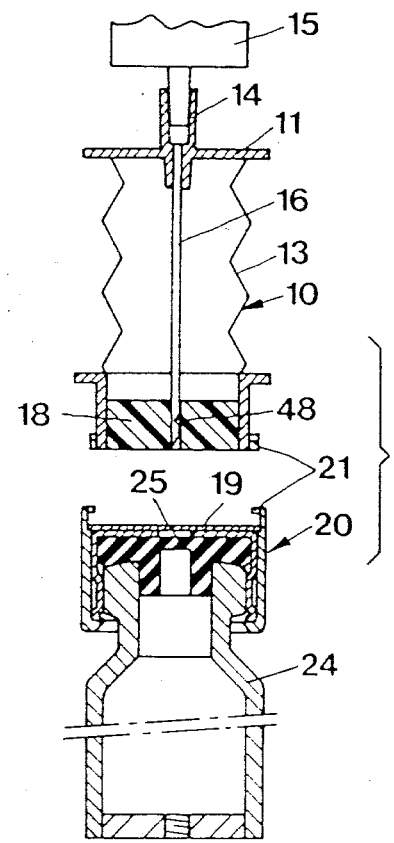

In FIG. 10 is shown a modified embodiment according to which the needle 16 is closed at the tip and provided with a radial opening 48 communicating with the passage of the needle. The first member 10 comprises a sealing member 18 in the form of a sleeve through which the needle 16 passes and which seals the opening 48 when the needle is in the position shown in FIG. 10. The second member 20 is attached to the ampoule 24 and has a bayonet coupling 21 for receiving the first member 10 in a position where the sleeve-shaped membrane 18 lies tight against the membrane 19. The needle 16 is passed through the sleeve 18 and membrane 25 and into the ampoule 24 by pressing together the flexible side walls 13 of the first member 10. The mobility of the needle 16 with respect to the sleeve 18 and membrane 19 can of course be achieved in other ways too.

Figure 11:
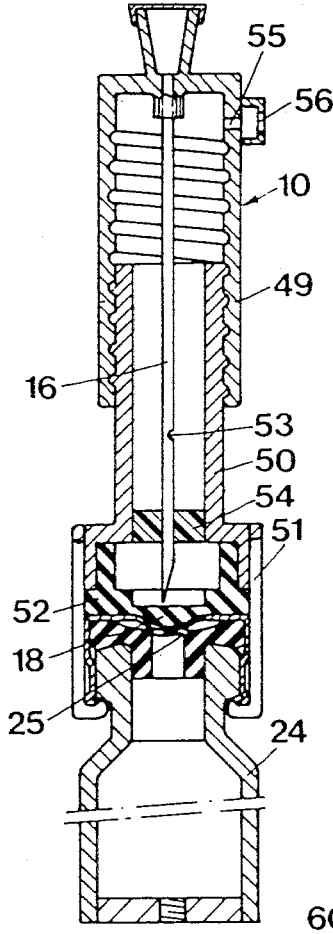

In the embodiment shown in FIG. 11 the first member comprises two parts 49, 50 threaded into each other, the needle 16 being attached to the outer part 49 and the first membrane 18 to the inner part 50. Said inner part 50 is further provided with coupling means in the form of gripping arms 51 intended to grip about the bottle-neck of the first vessel 24. In this case the first membrane 18 makes a unit with a resilient stopper 52 at the free end of said inner part 50. When the first member 10 is coupled to the vessel 24 the first membrane 18 is pressed against the closure means of the vessel 24. The membrane 25 of the vessel makes said second membrane. The first membrane 18 has a convex sealing surface in order to improve the sealing effect against the closure means of the vessel 24.

The needle 16 is provided with a radial opening 53, which in a certain position of the needle when this has penetrated the membranes 18 and 25 is closed by a sealing 54 in the first member and through which the needle passes. Preferably the needle 16 cannot be moved past said position. The substance in the vessel 24 can now be transferred through the needle 16 e.g. to an injection syringe. For ventilating or pressure equalizing the vessel 24 the needle is withdrawn a certain distance so that the radial opening 53 is exposed and admits the interior of the vessel 24 to communicate with the interior of the member 10. This is provided with a ventilating hole 55 covered by a liquid-rejecting filter 56. An expandable bladder (not shown) could of course be arranged to communicate with said hole 55 in order to provide a closed pressure-equalizing system.

Figure 4:
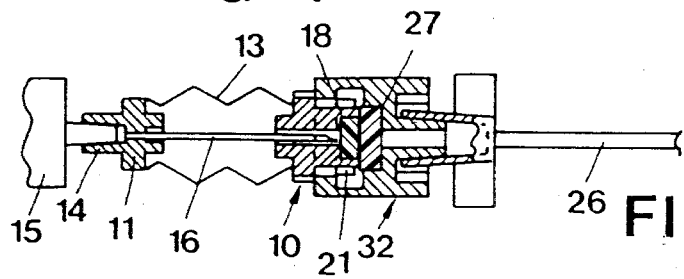
Figure 12:
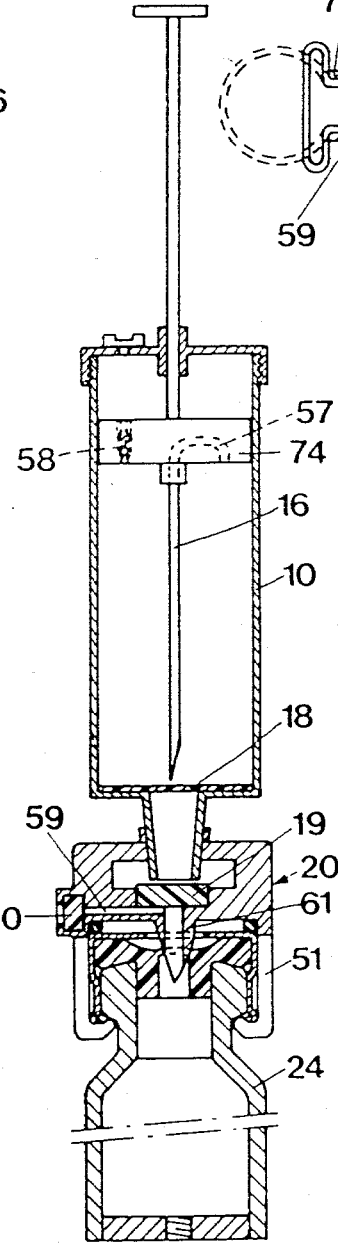

In the embodiment shown in FIG. 12 the first member 10 also makes the second vessel to which the substance is transferred. The needle 16 is provided with a piston guide 74 having a passage 57 connecting the interior of the member 10 with the passage of the needle 16. The piston guide 74 is further provided with a non-return valve 58, so that the it can be moved downwards towards the membrane 18. When moving the piston guide 74 and the needle 16 in the opposite direction a suction effect is provided in the member 10 at which the substance is sucked into the member 10 through the needle 16 and passage 57. The member can then be disconnected from the second member 20 and the substance be transferred to the intended application via a third member 32 (FIG. 4).

In this embodiment the second member 20 is provided with a pointed member 61 for penetrating the closure means (membrane 25) of the vessel 24. The pointed member 61 has a passage 62 through which the needle 16 can be passed and which further communicates with a ventilating passage 59 in the second member 20. Said ventilating passage is covered by a liquid-rejecting filter 60. The pointed member 61 is preferably made as an integral unit with the second member 20 of a plastic material.

Figure 13:
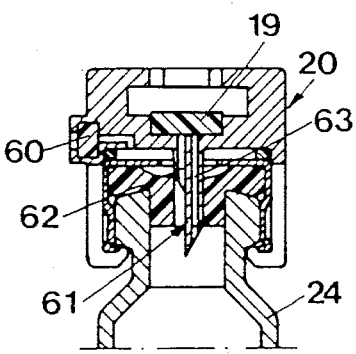

The embodiment of FIG. 13 differs from the one according to FIG. 13 through the design of the pointed member 61. This is provided with two passages one 62 for the needle 16 and the other 63 for ventilating the vessel 24. The inlet openings of the two passages are located so far from each other that the risk for sucking air into the needle 16 is eliminated.

Figure 14:
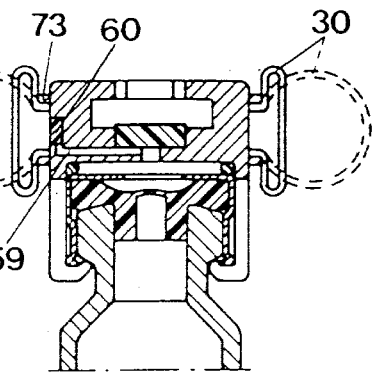

In the embodiment shown in FIG. 14 the second member 20 is provided with a ventilating passage 59 covered by a liquid-rejecting filter 60. Connection means 73 are provided on the member 20 for connecting a resilient bladder 30 or tube to the member 20 over the filter 60. If there are no poisonous vapours in the system the device could be used without bladder 30, which could be supplied as a separate unit and connected to the member 20 when substances with poisonous vapours are to be transferred.

Figure 15:
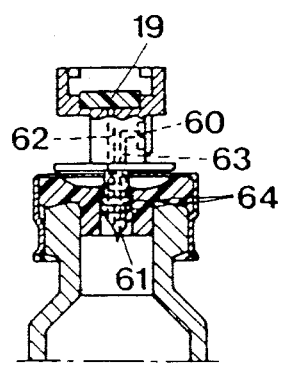

The pointed member 61 could make the coupling means for coupling the device 10, 20 to the vessel 24 as is shown in FIG. 15. In this case the pointed member 61 is provided with outwardly directed projections, e.g. barbs 64 for making the coupling safe.

In cases where the membrane of the vessel 24 makes the second membrane a pointed member 61 connecting the first member 10 to the second member could be provided with a line of weakness. For disconnecting the two members the pointed member 54 is simply broken off and sealed by being bent or otherwise squeezed together.

Figure 16:
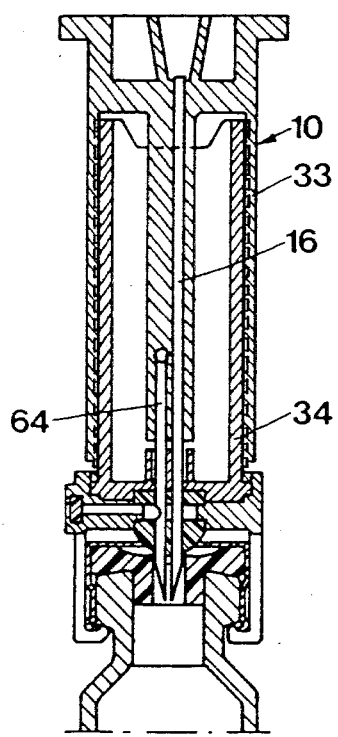

In the embodiment of FIG. 16 there are two puncturing members or needles 16 and 64 attached to the first member 10 and which both penetrate the membranes 18 and 19. The telescoping parts 33, 34 of the membrane 10 are unrotatably connected to each other. The second needle 64 comprises an open slotted needle or has a through passage with radial holes for providing a connection between the interior volume of the vessel 24 and the atmosphere via the filter 60 or to an expandable bladder covering this. The interior of the first member 10 could possibly also be ventilated through said second needle 64. The second membrane 19 in this embodiment has a convex contact surface for improving the sealing effect against the membrane of the vessel 24, which in this case makes the second membrane.

Figure 17:
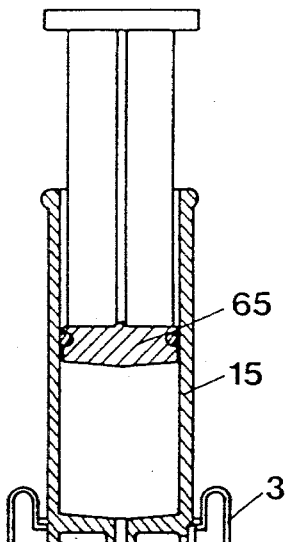

In FIG. 17 is shown a further embodiment wherein the first member 10 is in one piece with the second vessel 15, the piston of which is given the numeral 65. The member 10 comprises two parts 49 and 50 threaded into each other. The needle 16 is over portion near its free end surrounded by a further needle 66 attached to the needle and having a cutting edge at a angle to the cutting edge of the needle 16. Said angle preferably corresponds to the pitch of the threads of the treated members 49, 50 as the needles 16 and 66 are rotated through the membranes 18 and 25. The space between the two needles 16 and 66 admits ventilation of the vessel 24.

The gripping arms 51 for coupling the member 10 to the bottle-neck of the vessel 24 are pressed against this by tightening a nut 67.

Figure 18:
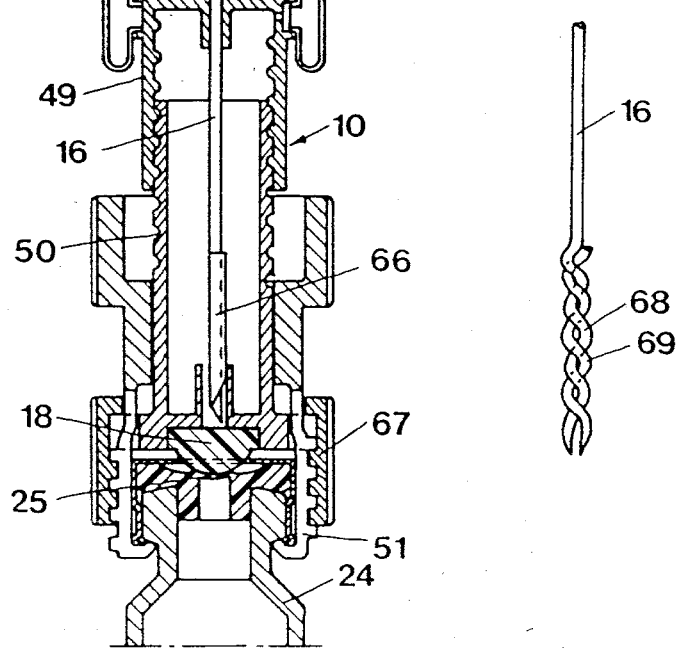

In FIG. 18 is shown a further variant of a needle 16 designed for being passed through the membranes by rotation. The needle 16 is at its end portion helical 68 and a second helical needle 69 is wound about said helical portion 68. The second helical needle 69 is provided with a through passage for ventilating the vessel 24. The pitch of the helical portion 68 and member 69 preferably corresponds to the pitch of the threads of the portions 49, 50 of the first member 10.

Figure 19:
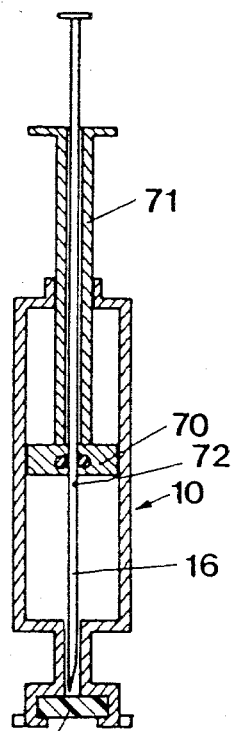

In FIG. 19 is shown a further embodiment in which the needle 16 is passed through a piston 70 slidingly received in the member 10, which also makes the second vessel to which the substance is transferred. The piston rod 71 is designed as a semi-cylindrical member, so that it is possible to manoeuvre the needle 16 from within said piston rod 71. A radial opening 72 is provided in the needle 16.

It would be possible to make the device without a needle, whereby the device is equipped with a membrane at the end remote from the membranes 18 and 19 through which a needle from an injection syringe can be passed. The device then functions in the same way as described above.

Several variants of the device according to the invention are of course possible within the scope of the claims. It would be possible to make the needle 16 displaceable in the device with a lever on its outside provided with an air sealing. The needle is then sealed against and guided by the inside of the first member by means of a piston guide or a collar portion.

In most of the embodiments shown the membranes 18 and 19 or 25 are brought to tight apposition against each other in the connected position of the members 10 and 20. This gives a sealing effect between a membranes and eliminates the risk for any leakage of the substance between the membranes. In some embodiments there is shown a certain distance between the membranes in the connected position of the members 10 and 20, which does not give the above sealing effect, but the risk for leakage between the membranes is small.

Other orientations of the membranes 18 and 19, 25 with respect to each other are of course possible within the scope of the claims. They need not to be located just opposite each other, the purpose is that they can be penetrated by the needle.

A plurality of modifications are possible and it should be pointed out that portions from the different embodiments can be replaced and combined with each other in many ways.

I claim:

1. A fluid transfer system for transferring a substance from a first vessel to a second vessel avoiding contamination, said system being attached or connectible to said first vessel or a cover enclosing the first vessel, comprising:

(1) a first member hermetically enclosing a puncturing member provided with a passageway, said first member having a first sealing member for being passed and retracted therethrough, at which the sealing effect of said sealing member is maintained after retraction of the puncturing member;

(2) a second member having a second sealing member; mating connection means arranged on said first and second members for providing a releasable locking of said members with respect to each other, said sealing members in the connected position of the first and second members being located in a position with respect to each other so that they can be penetrated by the puncturing member, wherein after transfer of said substance the puncturing member is retractable to a position in which said puncturing member is hermetically enclosed in said first member and the first and second members are disconnectable from each other.

2. The device according to claim 1 wherein said sealing members in the connected position of the first and second members are brought to tight apposition against each other.

3. The device according to claim 2 wherein said first vessel has a closure means and said second member forms a unit with said closure means of the first vessel.

4. The device according to claim 3 wherein said first member is so designed that the distance between the first sealing member and the attachment for the puncturing member can be lengthened and shortened.

5. The device according to claim 4, wherein the first member has flexible side walls whereby through pressing the walls together in the axial direction of the puncturing member, said puncturing member passes through the sealing members.

6. The device according to claim 5, wherein the puncturing member is displaceably arranged in the first member and guided along the inside thereof.

7. The device according to claim 6, wherein the first member further comprises a cylinder and the puncturing member provided with a ventilated piston guide slidingly received within said cylinder, the puncturing member being attached to a connection piece arranged to firmly receive said second vessel and a seal is formed between the puncturing member and the interior of said cylinder.

8. The device according to claim 5, wherein the first member further comprises a pair of outer and inner telescoping parts the puncturing member being attached to one telescoping part and the first sealing member being attached to the other telescoping part.

9. The device according to claim 8, wherein the outer telescoping part comprises means for firmly receiving said second vessel, the puncturing member being attached to said outer part and said first sealing member being attached to the inner part, a seal being provided between the interior of the inner part and the outer part and air being admitted to pass between the inside of the outer part and the outside of the inner part, said inner and outer parts being undetachably and unrotatably connected to each other at least in the most extended position.

10. The device according to claim 5, wherein the first member further comprises a pair of parts threaded into each other, the puncturing member being attached to one part and the first sealing member being attached to the other part.

11. The device according to claim 5, wherein the puncturing member is displaceably arranged in the first member by a lever manouverable from the outside thereof.

12. The device according to claim 11, wherein said first sealing member is in the form of a sleeve through which the puncturing member is passed and which in one position is arranged to cover a radial opening in a needle communicating with the transmission channel thereof, the tip of the needle being closed and the needle being movable with respect to said sealing member to a position where the radial opening is exposed.

13. The device according to claim 12, wherein the puncturing member is provided with a radial opening so that the interior of the first vessel can communicate with the interior of the first member in a certain position of the puncturing member and that a sealing is provided for closing said radial opening in a second certain position of the puncturing member.

14. The device according to claim 13, wherein the passage of the puncturing member is arranged to communicate with the interior volume of said first member which makes said second vessel.

15. The fluid transfer system according to claim 1, wherein one end of the second member is attached or connectible to a cannula, a vein catheter, or an infusion device and the opposite end of said second member is connectible to the first member.

16. The device according to claim 15, wherein the device is provided with coupling means arranged to be connected to said first vessel about the bottle-neck thereof.

17. The device according to claim 16, wherein the device is provided with coupling means arranged to be connected to said first vessel in a cavity in a closure means thereof.

18. The device according to claim 17, wherein an expandable bladder is arranged to communicate with the interior of the first vessel for pressure equalization when transferring a substance.

19. The device according to claim 18, wherein said device is provided with a pointed member having a passage therethrough and which can be passed through the closure means of the first vessel, at which the puncturing member is arranged to be passed through said pointed member into the first vessel.

20. The device according to claim 19, wherein said pointed member has a passage communicating with the atmosphere via a liquid-rejecting filter or with an expandable bladder for ventilating the first vessel.

21. The device according to claim 20, wherein said pointed member makes the coupling means for connecting the device to said first vessel.

22. The device according to claim 21, wherein two substantially parallel puncturing members are arranged to pass through the first and second sealing members, one of said puncturing members being arranged to transfer the substance to said second vessel and the second being provided with a passage for ventilating the interior of the first vessel when said second puncturing member is passed through the second sealing member.

23. The device according to claim 22, wherein said passage of said second puncturing member is arranged to ventilate the interior of the first member.

24. The device according to claim 23, wherein the puncturing member over a portion near its free end is surrounded by a further puncturing member attached to the first puncturing member, at which there is a free space between the two puncturing members arranged to ventilate the interior of the first vessel.

25. The device according to claim 10, wherein the puncturing member has a helical end portion a second helical puncturing member being wound about said end portion, said second helical puncturing member having a passage therethrough arranged to ventilate the interior of the first vessel.

26. The device according to claim 25, wherein the pitch of said helical portion and helical puncturing member corresponds to the pitch of thread of the threaded portions of the first member.

27. The device according to claim 26, wherein the first sealing member has a convex sealing surface.

* * * * *